(12) United States Patent
Schmitt-Bylandt

(10) Patent No.: US 8,899,237 B2
(45) Date of Patent: Dec. 2, 2014

(54) MOUTH TRAY

(76) Inventor: Juergen Schmitt-Bylandt, Gelnhausen-Haitz (DE)

(*) Notice: Subject to any disclaimer, the term of this patent is extended or adjusted under 35 U.S.C. 154(b) by 0 days.

(21) Appl. No.: 13/293,187

(22) Filed: Nov. 10, 2011

(65) Prior Publication Data

US 2012/0055489 A1 Mar. 8, 2012

Related U.S. Application Data

(63) Continuation of application No. PCT/DE2011/001229, filed on Jun. 3, 2011.

(30) Foreign Application Priority Data

Jun. 9, 2010 (DE) .......................... 10 2010 023 256

(51) Int. Cl.
A61C 5/14 (2006.01)
A61C 3/00 (2006.01)
A61F 5/56 (2006.01)

(52) U.S. Cl.
CPC .. *A61C 5/14* (2013.01); *A61F 5/566* (2013.01)
USPC .............................................. 128/861; 433/6

(58) Field of Classification Search
USPC ............ 128/846, 857, 859, 861; 433/2, 8, 10, 433/13, 15, 6, 23, 24
See application file for complete search history.

(56) References Cited

U.S. PATENT DOCUMENTS

| | | | | |
|---|---|---|---|---|
| 4,727,867 A | * | 3/1988 | Knoderer | 128/859 |
| 4,815,972 A | * | 3/1989 | Howe | 433/5 |
| 5,879,155 A | | 3/1999 | Kittelsen | |
| 6,200,133 B1 | * | 3/2001 | Kittelsen | 433/6 |
| 6,660,029 B2 | * | 12/2003 | VanSkiver et al. | 607/113 |

FOREIGN PATENT DOCUMENTS

| | | |
|---|---|---|
| DE | 295 09 294 | 10/1995 |
| KR | 10 2004 008 6888 | 10/2004 |
| WO | WO 03/011362 | 2/2003 |

OTHER PUBLICATIONS

English translation of KR1020030017987.*
International Search Report of PCT/DE2011/001229, Jul. 18, 2012.
International Preliminary Report on Patentability of PCT/DE2011/001229, Dec. 10, 2012.

* cited by examiner

*Primary Examiner* — Patricia Bianco
*Assistant Examiner* — Tarla Patel
(74) *Attorney, Agent, or Firm* — Collard & Roe, P.C.

(57) ABSTRACT

A mouth tray includes a wire-like element onto which two bite elements are attached. The element is formed of two U-shaped bows, the arms of which are connected to each other. The bite elements are each attached on the arm-side transitions between the two bows.

11 Claims, 1 Drawing Sheet

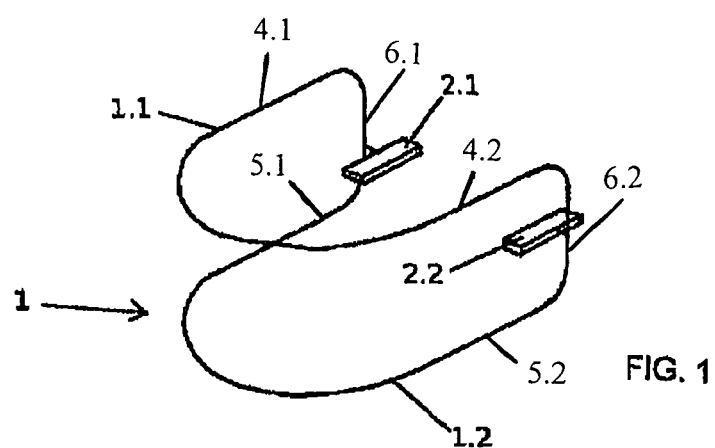
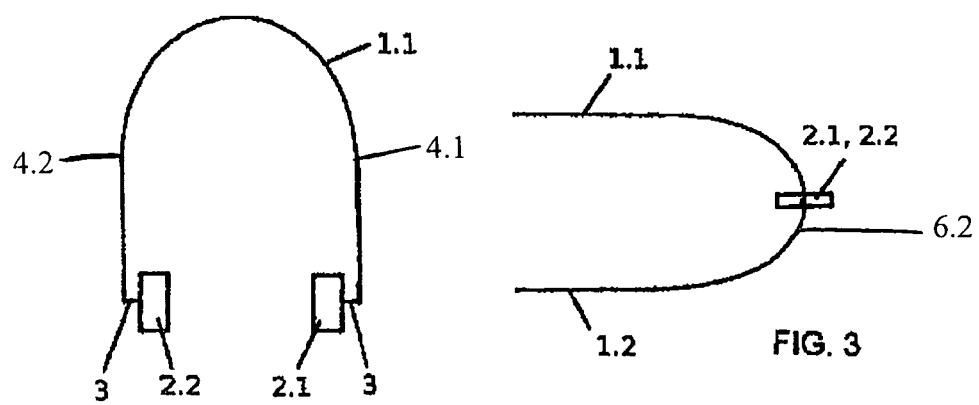

MOUTH TRAY

CROSS REFERENCE TO RELATED APPLICATIONS

Applicant claims priority under 35 U.S.C. §119 of German Application No. 10 2010 023 256.4 filed Jun. 9, 2010. Applicant also claims priority and this application is a continuation under 35 U.S.C. §120 of International Application No. PCT/DE2011/001229 filed Jun. 3, 2011, which claims priority under 35 U.S.C. §119 of German Application No. 10 2010 023 256.4 filed Jun. 9, 2010. The international application under PCP article 21(2) was not published in English. The disclosures of the aforesaid International Application and German Applications are incorporated herein by reference.

BACKGROUND OF THE INVENTION

1. Field of the Invention

The invention relates to a mouth tray including a wire-like element onto which two bite elements are attached.

2. The Prior Art

A mouth tray of the type described above is known from DE 255 09 294 U1. It comprises a wire-like element (referred to therein as a connection member), to which two bite elements (referred to as a chew part) are attached. The connection member is typically made of stainless steel or titanium. The chew parts are made of plastic. In the same way as in the invention to be explained below, the chew parts or bite elements are intended to be arranged between the human molars of the upper and lower jaw in order to protect the teeth from the effects of grinding the teeth, biting the cheek or suchlike.

The chow parts in accordance with the solution according to DE 295 09 294 U1 are largely fitted flush to the molars of the upper and lower jaw. In the labial and buccal region the connection member connecting the chew parts with each other runs between the gums of the front teeth and the upper and/or lower lip.

The aim of the invention is to improve a mouth tray of the type cited in the introduction.

SUMMARY OF THE INVENTION

This aim is achieved with a mouth tray including a wire-like element onto which two bite elements are attached, wherein the element is formed of two U-shaped bows, the arms of which are connected to each other and wherein the bite elements are each attached on the arm-side transitions between the two bows.

According to the invention it is also envisaged that the element is formed of two U-shaped bows the arm of which are connected to each, and in that the bite elements are in each case attached On the arm-side transitions between the two bows.

In other words, in accordance with the invention and in contrast to the aforementioned DE 295 09 294 a total of two U-shaped bow are envisaged. When the mouth tray is being worn one of the bows is in the labial and buccal area (also known as buccolabial fold) of the lower jaw and the other is in the labial and buccal area of the upper jaw. The bows are connected to each other on the arm side by way of appropriately designed connection areas or transitions, whereby it is preferably envisaged that both bows and the transitions are produced in one piece from wire, more particularly a nickel-titanium wire coated with plastic. The transitions, which when being worn, are located in the vicinity of the mandibular joint (i.e. facing away from the incisors) are preferably also U-shaped, i.e. seen abstractly the mouth tray comprises four U-shaped sections, whereby two sections form the U-shaped bows and the two others, preferably also U-shaped sections, form said transitions which run perpendicularly to the bows.

Overall, in this way a very elastic mouth tray is produced, which when being worn is on the one hand positioned in both labial and buccal areas of the upper and lower jaw and on on the other hand on which the bite elements are attached in the area of the transitions. The fact that this mouth tray is very comfortable to wear is combined with the advantage that the mouth can be opened and closed without hindrance and without the risk of the bite elements falling out of the mouth. If the mouth is opened, the bite elements are to a certain extent "suspended" on the transitions between the molars (without being firmly attached to the teeth as in DE 295 09 294) so that they automatically re-assume the correct position as soon as the mouth is closed.

The feature "wire-like" expresses the fact that the bows, as stated, are preferably, but not necessarily, made of metal. Also conceivable is the use of bows made of plastic, which are designed to be appropriately narrow and elastic so as to be taken up in the relevant labial and buccal area.

Other advantageous further embodiments of the mouth tray in accordance with the invention are set out in the dependent claims.

For the sake of completeness reference is also made to the following two documents:

From WO 2003/011362 A2 a therapeutic mouth tray is known which is used to heat or cool mouth tissue. This mouth tray does not have a bite element.

From KR 10 2004 008 6888 A a mouth tray is known which is provided with two "acting agent storing units". Simply with regard to their arrangement on the carrier element (this is evidently deliberately selected so that the user cannot bite on them) these units for holding an active agent (for example for treating bad breath) do not correspond with the bite elements in accordance with the invention.

BRIEF DESCRIPTION OF THE DRAWINGS

The mouth tray in accordance with the invention including its advantageous further developments in accordance with the dependent claims will be explained in more detail below with the aid of the drawing of an example of embodiment.

Schematically

FIG. 1 shows a perspective view of the mouth tray in accordance with the invention;

FIG. 2 shown a view from above of the mouth tray in accordance with the invention; and FIG. 3 shows a side view of the mouth tray in accordance with the invention.

DETAILED DESCRIPTION OF PREFERRED EMBODIMENTS

As is known the mouth tray in accordance with the invention shown in FIGS. 1 to 3 comprises a wire-like element 1 onto which two bite elements 2.1, 2.2. are fastened in a non-rotational manner.

Essential to the mouth tray in accordance with the invention is that element 1 is formed of two U-shaped bows 1.1, 1.2 both arms 4.1, 4.2 and 5.1, 5.2 of which are connected to each other and that the bite elements 2.1, 2.2 are each attached to arm-side transitions 6.1, 6.2 between the two bows 1.1, 1.2.

The two U-shaped bows 1.1, 1.2 as well as the transitions 6.1, 6.2 are designed in such a way that when the mouth is open the mouth tray remains in both buccolabial folds with a certain degree of pre-tensioning and are therefore self-stabilising.

As stated in the introduction, the U-shaped, wire-like bows 1.1, 1.2 can in principle also be made of plastic, however it is particularly envisaged that the bows 1.1, 1.2 are made of metal, more especially nickel-titanium.

In order to prevent the metal cutting into the oral mucous membrane and a feeling of choking, as well as to distribute the load better overall and thereby further increase wearing comfort, in accordance with the invention it is envisaged (not additionally shown) that the metallic bows 1.2, 1.2 are provided with a coating, preferably made of plastic.

In order to be able to produce the mouth tray in accordance with the invention with as few components as possible, it is also envisaged, as shown in the figures, that the bows 1.1, 1.2 and the arm-side transitions 6.1, 6.2 are made of one piece, for example, of a piece of nickel-titanium wire (only connected at one point).

In order to avoid sharp edges and to thereby further increase the wearing comfort the arm-side transitions 6.1, 6.2 are U-shaped, whereby (see in particular FIG. 1) it is particularly preferably envisaged that the U-shaped bows 1.1, 1.2 and the U-shaped arm-side transitions 6.1, 6.2 are arranged offset at 90° to each other.

A design of the transitions is also conceivable (not shown) in which they are riot only U-shaped, but are spiral or loop-shaped as part of a screw. This form further increases the flexibility of the mouth tray and at the same time results in further stabilisation of the position of the tray in the mouth.

To fasten the bite elements 2.1, 2.2 to the wire-like element 1, as shown in FIG. 2 in particular, a holding element 3 is arranged on each arm-side transition 6.1, 6.2. This is preferably also wire-like and connected in one piece with the arm-side transition 6.1, 6.2. More particularly it is envisaged (not additionally shown) to form the holding element 3 from the wire of the arm-side transition 6.1, 6.2 so that the bows 1.1, 1.2, the transitions 6.1, 6.2 and the holding element 3 are all formed from one single piece of wire which only has to be joined at one point, preferably thermally, more particularly through welding.

With regard to the bite elements 2.1, 2.2 it is envisaged that with regard to the U-shaped bows 1.1, 1.2 they (see FIGS. 1 and 2) are arranged pointing into the interior of the bows 1.1, 1.2 and are optionally made of plastic or rubber. In addition to their purely supportive and/or mandibulular joint-relieving . function it it finally advantageously envisaged to design the bite elements 2.1, 2.2 for dental treatment, for example as fluid-saturated sponge or depot-like, possibly also slowly dissolving medication carriers.

LIST OF REFERENCE SYMBOLS

1 Wire-like element
1.1 U-shaped bow
1.2 U-shaped bow
2.1 Bite element
2.2 site element
3 Holding element

What is claimed is:

1. A mouth tray comprising:
    a wire-like element formed by:
        a top U-shaped bow comprising a first top arm and a second top arm connected to the first top arm,
        a bottom U-shaped bow comprising a first bottom arm and a second bottom arm connected to the first bottom arm,
        a first arm-side transition area connecting the top U-shaped bow and the bottom U-shaped bow, and
        a second arm-side transition area connecting the top U-shaped bow and the bottom U-shaped bow,
        a first bite element attached to the first arm-side transition area, and
        a second bite element attached to the second arm-side transition area,
    wherein the first transition area and the second transition area are configured such that when the mouth tray is worn by a user the bite elements are arranged parallel to a chewing plane between molars of an upper jaw and a lower jaw of the user to permit the user to bite on the bite elements.

2. The mouth tray in accordance with claim 1, wherein the top and bottom U-shaped bows are made of metal.

3. The mouth tray in accordance with claim 2, wherein the top and bottom U-shaped bows are provided with a coating.

4. The mouth tray in accordance with claim 2, wherein the top and bottom U-shaped bows are made of nickel-titanium.

5. The mouth tray in accordance with claim 1, wherein the top and bottom U-shaped bows and the first and second arm-side transitions are formed as one piece.

6. The mouth tray in accordance with claim 1, wherein the first and second arm-side transitions are each U-shaped.

7. The mouth tray in accordance with claim 6, wherein the top and bottom U-shaped bows and the first and second arm-side transitions are arranged offset at 90° to each other.

8. The mouth tray in accordance with claim 1, further comprising:
    a first holding element for the first bite element and arranged on the first arm-side transition, and
    a second holding element for the second bite element and arranged on the second arm-side transition.

9. The mouth tray in accordance with claim 1, wherein the first and second bite elements are each arranged facing into an interior of the top and bottom U-shaped bows.

10. The mouth tray in accordance with claim 1, wherein the first and second bite elements are made of plastic or rubber.

11. The mouth tray in accordance with claim 1, wherein the first and second bite elements are formed as medication carriers.

* * * * *